(12) United States Patent
Schultz et al.

(10) Patent No.: US 6,589,316 B1
(45) Date of Patent: Jul. 8, 2003

(54) SMOKE EVACUATION SYSTEM

(76) Inventors: Leonard S. Schultz, 11036 Boone Cir., Bloomington, MN (US) 55438; Jeffrey K. Drogue, 5117 Washburn Ave. South, Minneapolis, MN (US) 55410

( * ) Notice: Subject to any disclaimer, the term of this patent is extended or adjusted under 35 U.S.C. 154(b) by 0 days.

(21) Appl. No.: 09/544,695

(22) Filed: Apr. 7, 2000

Related U.S. Application Data

(63) Continuation-in-part of application No. 09/046,265, filed on Mar. 23, 1998, now Pat. No. 6,110,259.
(60) Provisional application No. 60/066,331, filed on Nov. 21, 1997.

(51) Int. Cl.[7] .......................... B01D 39/00; B01D 50/00
(52) U.S. Cl. .......................... 95/273; 55/385.1; 55/503; 604/35
(58) Field of Search ..................... 55/385.1, 385.2, 55/418, 486, 503, 505, 385.4; 604/33, 45, 264; 95/273, 286

(56) References Cited

U.S. PATENT DOCUMENTS

| | | |
|---|---|---|
| 3,952,727 A | 4/1976 | Nolan |
| 4,083,706 A | 4/1978 | Wiley |
| 4,211,224 A | 7/1980 | Kubach et al. |
| 4,294,594 A | 10/1981 | Sloane, Jr. et al. |
| 4,449,970 A | 5/1984 | Bevan et al. |
| 4,451,258 A | 5/1984 | Jensen |
| 4,735,603 A | 4/1988 | Goodson et al. |
| 4,874,513 A | 10/1989 | Chakraborty et al. |
| 4,906,261 A | 3/1990 | Mohajer |
| 4,963,134 A | 10/1990 | Backscheider et al. |
| 4,986,839 A | 1/1991 | Wertz et al. |
| 5,199,944 A | 4/1993 | Cosmescu |
| 5,242,474 A | 9/1993 | Herbst et al. |
| 5,423,779 A | 6/1995 | Yeh |
| 5,578,000 A | 11/1996 | Greff et al. |
| 5,597,385 A | 1/1997 | Moerke |
| 5,626,568 A | 5/1997 | Yeh et al. |
| 5,674,219 A | 10/1997 | Monson et al. |
| 5,688,256 A * | 11/1997 | Surratt et al. ............... 604/355 |
| 5,709,675 A | 1/1998 | Williams |
| 5,722,962 A * | 3/1998 | Garcia ........................ 604/264 |
| 5,779,662 A | 7/1998 | Berman |
| 5,824,138 A | 10/1998 | Taylor, III |

OTHER PUBLICATIONS

Carter, James E., MD, PhD, FACOG. *Laparoscopy in the Millennium, New Interdisciplinary Courses Bring Laparoscopists Together, The SLS Report* 2000 Fall; 9(2): 2.
*Orlando 2000, The SLS Report* 2000 Fall; 9(2): 4.
*Scientific Presentations: Sampling from the over 200 Abstracts to be presented at Endo Expo 2000, The SLS, Report* 2000 Fall; 9(2): 8.
*Porous Media Vindicates Damaged Reputation Caused By Pall Corporation*, 1997, Advertisement.

* cited by examiner

*Primary Examiner*—Robert A. Hopkins
(74) *Attorney, Agent, or Firm*—Dorsey & Whitney LLP

(57) ABSTRACT

A smoke evacuating system for use during surgical procedures, particularly minimally invasive procedures involving the use of a laser or cautery at a surgical site having an associated higher than ambient pressure, wherein the system includes a filter with a site side and an outlet side and a fluid conduit extending between the surgical site and the filter. The filter includes a filter media and a housing substantially surrounding the filter media with a space between the filter media and the housing to collect condensed vapor. The filter exhibits low resistance or a low pressure drop and resists fluid flow, whereby the higher than ambient pressure is not substantially diminished and generates a fluid flow in the fluid flow path tending to carry smoke to and through the filter.

12 Claims, 4 Drawing Sheets

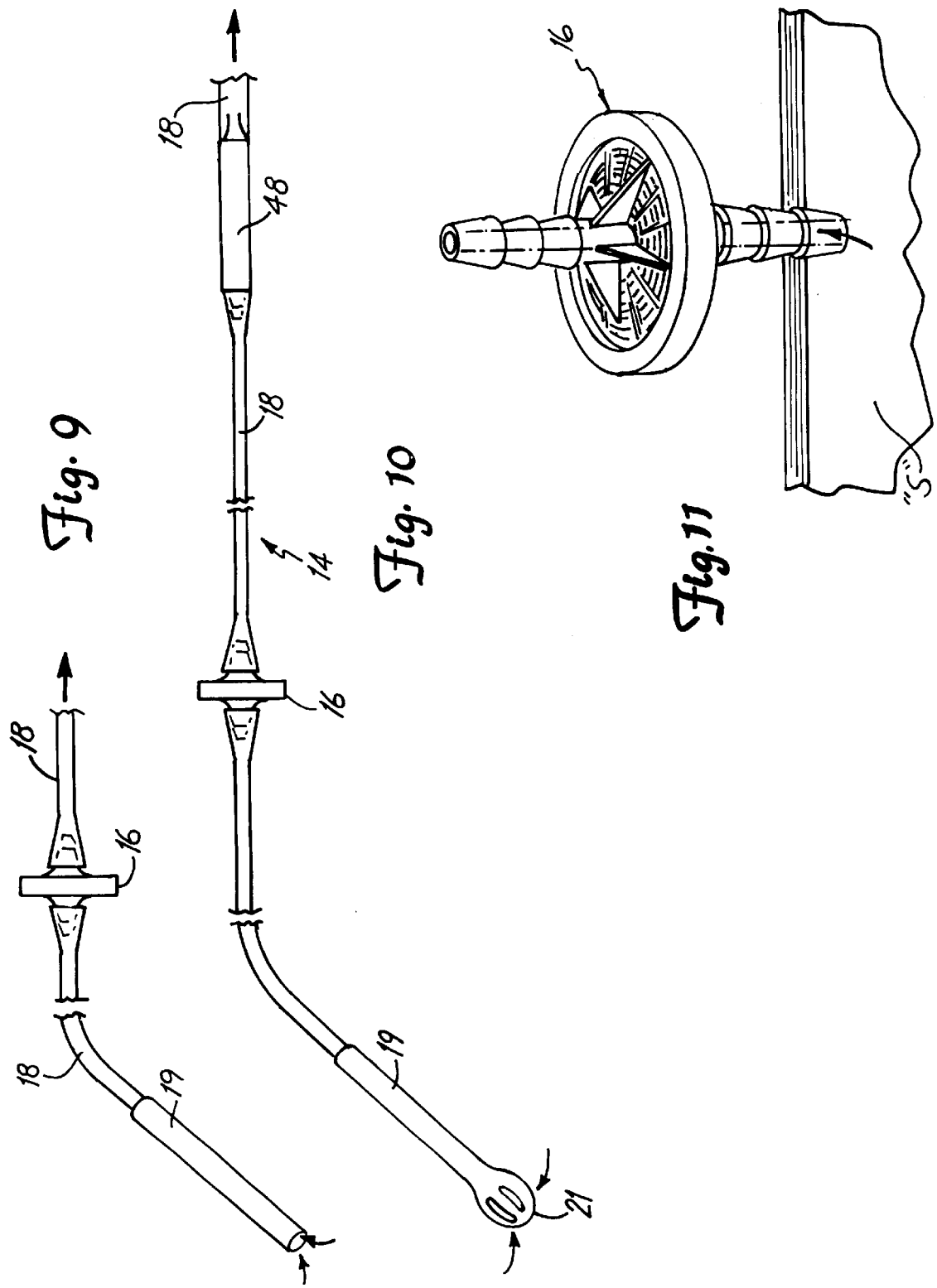

SMOKE EVACUATION SYSTEM

The present application is a continuation-in-part of co-pending U.S. application Ser. No. 09/046,265, filed Mar. 13, 1998, now U.S. Pat. No. 6,110,259, which claims the priority benefit of a U.S. provisional application, Ser. No. 60/066,331, filed Nov. 21, 1997.

FIELD

The present invention relates to smoke removal and filtering and, more particularly, to a smoke evacuation system for use in surgical procedures, including minimally invasive surgical procedures such as laparoscopy, during which cautery or a laser is used.

BACKGROUND

U.S. Pat. No. 5,578,000 (Greff et al.) discloses a smoke evacuation system including a trocar having a working channel, a stopcock or valve communicating with the channel, a source of wall vacuum, a fluid conduit connected between the stopcock of the trocar and the source of wall vacuum, a first filter for applying a first reduction in suction and separating smoke into its components and a residual gas, and a flow restriction to generate a second reduction in suction. The flow restriction is along a passage formed by the conduit, the filter and working channel.

Greff et al. note that smoke has been handled by simply allowing it to escape into the operating room, thereby subjecting the surgeon and staff to contaminants. They recognize that closed, recirculating systems involving two trocars have been used, as have probes which are inserted through a trocar, but that such systems do not adequately solve the problems associated with smoke and the removal thereof, e.g., contamination, smell and impaired visibility of a surgical site.

Other problems inadequately addressed by currently available evacuation systems are loss of the pressure in the pneumoperitoneum, and/or tissue drying, particularly if pressure loss is compensated for by increasing insufflation gas flow.

While the smoke evacuation system disclosed in the Greff et al. patent may be well suited for its intended purpose, it would be advantageous if the dependency on a remote, "in-wall" vacuum source could be eliminated thereby reducing the cost and complexity of the system.

SUMMARY

The present invention provides an improvement over currently known smoke evacuation systems, methods and techniques, including laparoscopic smoke evacuation systems such as the system disclosed in the Greff et al. patent.

In one embodiment, the present invention provides a smoke evacuating system for use during surgical procedures comprising a filter for operable coupling to a surgical site, said filter exhibiting a pressure drop ranging from approximately 0.5 to 20 mm/Hg, with a preferred pressure drop ranging from approximately 1 to 3 mm/Hg. The filter may be coupled directly to the patient.

In another embodiment, the present invention provides a smoke evacuating system for use during surgical procedures, particularly minimally invasive procedures, involving a surgical site having an associated higher than ambient pressure, wherein the system comprises a filter with a inlet side (the side generally closest to the surgical site) and an outlet side and a fluid conduit extending between the surgical site and the filter. The fluid conduit defines a substantially unobstructed fluid flow path between the surgical site and filter, and the higher than ambient pressure and a pressure drop associated with the filter generate and enable a fluid flow in the fluid flow path, the filter causing a low pressure drop (i.e., pressure differential from side to side) in the fluid flow from the inlet side to the outlet side.

In yet another embodiment, the present invention provides a smoke evacuating system for use during surgical procedures, particularly minimally invasive procedures, including a conduit for operable coupling to a surgical site, said conduit operably carrying a filter exhibiting a pressure drop ranging from approximately 1 to 3 mm/Hg and defining a substantially unobstructed fluid flow path between the surgical site and the filter. The conduit may include a connector for being connected to a trocar or other tubular member. An on/off valve may be incorporated to control the flow of fluid through the conduit, whereby, when the valve is open, the flow path from the surgical site to the filter is substantially unobstructed.

An advantage of the present invention is that it eliminates dependency on a built-in, in wall vacuum source. It does not require high vacuum suction and the requisite high resistance filters or combination of flow restrictors or reducers and filters. Further, it simplifies smoke evacuation and filtering by eliminating the need for multiple, in-line structures (filters, resistors, etc.) for stepping down or reducing suction.

While the present invention may be used in surgical procedures, it may also be used in industry to remove smoke and/or chemicals from areas such as workstations. For example, it might be used at or adjacent to chip or electronic equipment manufacturing stations to reduce workers'0 exposure to smoke produced as connections are formed. Similarly, it might be used to reduce exposure to etching chemicals.

A feature of the present invention is a balanced smoke evacuation system wherein a filter with a relatively low pressure drop performs a filtering function and a flow regulating function, helping to preserve the pressure at or in a pressurized surgical site such as a laparoscopy with a pneumoperitoneum while providing for sufficient flow therefrom to remove smoke from the site, thereby reducing the need for substantial or constant reinsufflation of the surgical site.

Surgical aerosols, or bio-aerosols, include smoke from burning tissue, but also often include moisture, steam or mist produced by cells as they are heated and/or ruptured by certain surgical instruments such as lasers or ultrasonic scissors (e.g., "Harmonic Scissors" by Ethicon). Additionally, some surgeons are now using heated, humidified gas for insufflation to help maintain a normal body temperature and to help reduce tissue dessication. One embodiment of the invention is adapted for use in surgical procedures during which surgical aerosols, particularly moist or moisture containing aerosols, are produced and/or in which heated and/or humidified gas is used by including a space or region into which moisture can move, gather and/or be collected without diminishing flow rate or the efficiency of the filter.

Another embodiment of the invention includes an elbow member adapted to be coupled between a trocar and the conduit to position the conduit to reduce any potential inconvenience to the surgeon and/or staff during a procedure.

An advantage of the smoke evacuation system of the present invention is that it provides for the intra-operative or intra-procedural evacuation and filtration of smoke from a pressurized surgical site, e.g., the abdominal cavity, without requiring suction and without rapidly exhausting the pressurizing gas or causing a substantial pressure reduction at the pressurized surgical site. Other advantages are that the invention does not require an operator, it continuously removes smoke from the pressurized cavity (once the valve in valved embodiments is opened) to improve visibility without venting, it reduces operating time, it eliminates surgical smoke from the operating room, thereby reducing the health risk stemming from exposure to such smoke, it eliminates the need to apply suction to a patient thereby reducing potential tissue damage, and it is inexpensive.

Other features and advantages of the smoke evacuating apparatus and method of the present invention will become more fully apparent and understood with reference to the following description and drawings, and the appended claims.

BRIEF DESCRIPTION OF THE DRAWINGS

FIG. 9 depicts another embodiment of the smoke evacuation system of the present invention.

FIG. 10 depicts another embodiment of the smoke evacuation system of the present invention.

FIG. 11 depicts the filter of one embodiment of the present invention coupled to a surgical site.

DESCRIPTION

The accompanying Figures depict embodiments of the smoke evacuation apparatus or system of the present invention, and features and components thereof. With regard to means for fastening, mounting, attaching or connecting the components of the present invention to form the apparatus as a whole, unless specifically described otherwise, such means are intended to encompass conventional fasteners such as machine screws, machine threads, snap rings, hose clamps such as screw clamps and the like, rivets, nuts and bolts, toggles, pins and the like. Components may also be connected by friction fitting, or by welding or deformation, if appropriate. Unless specifically otherwise disclosed or taught, materials for making components of the present invention are selected from appropriate materials such as metal, metallic alloys, natural or synthetic fibers, plastics and the like, and appropriate manufacturing or production methods including casting, extruding, molding and machining may be used. The components of the invention may be constructed from any such suitable materials for use in surgical rooms or in surgical procedures.

Any references to front and back, right and left, top and bottom, upper and lower, and horizontal and vertical are intended for convenience of description, not to limit the present invention or its components to any one positional or spacial orientation.

Figure 1:
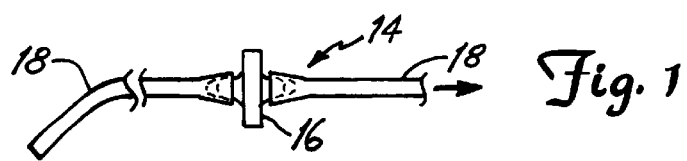
FIGS. 1 depicts one embodiment of the smoke evacuation system of the present invention.
Figure 5:
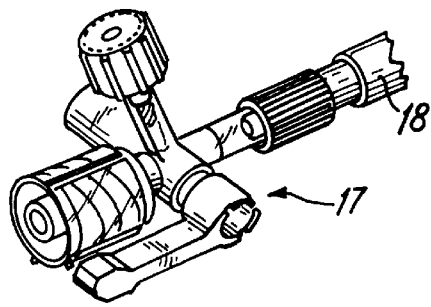
FIG. 5 depicts a connector stopcock or valve for use in the smoke evacuation system of the present invention.
Figure 8:
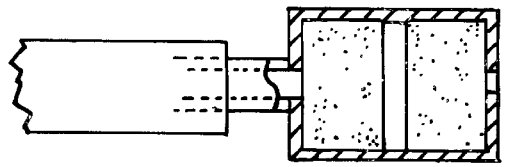
FIG. 8 depicts another embodiment of the filter.
Figure 2:
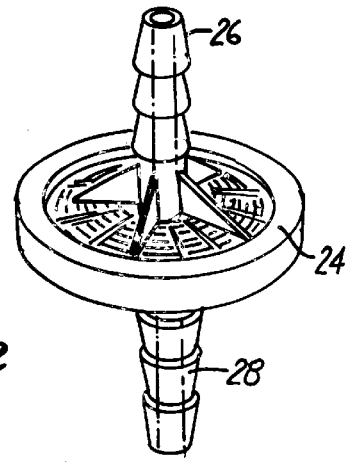
FIG. 2 depicts the filter of one embodiment of the present invention.

Referring to the Figures, particularly FIG. 1, the present invention provides a smoke evacuating system 14 for use during surgical procedures. The system 14 includes a filter 16 and a generally flexible fluid conduit 18 connected to the filter 16. The conduit 18 may be provided in one or more pieces. The system 14, particularly the end of the conduit 18, may include an integral or attachable male or female connector (of the type well known in the art) for facilitating the connection of the conduit 18 to the exhaust port or vent valve of a trocar, or the system 14 may include a Leur lock-type valve 17 (see FIG. 5) operably coupled to the conduit 18, and it may include a generally tubular member 20, such as a typical well known trocar with an exhaust port (not shown).

Figure 3:
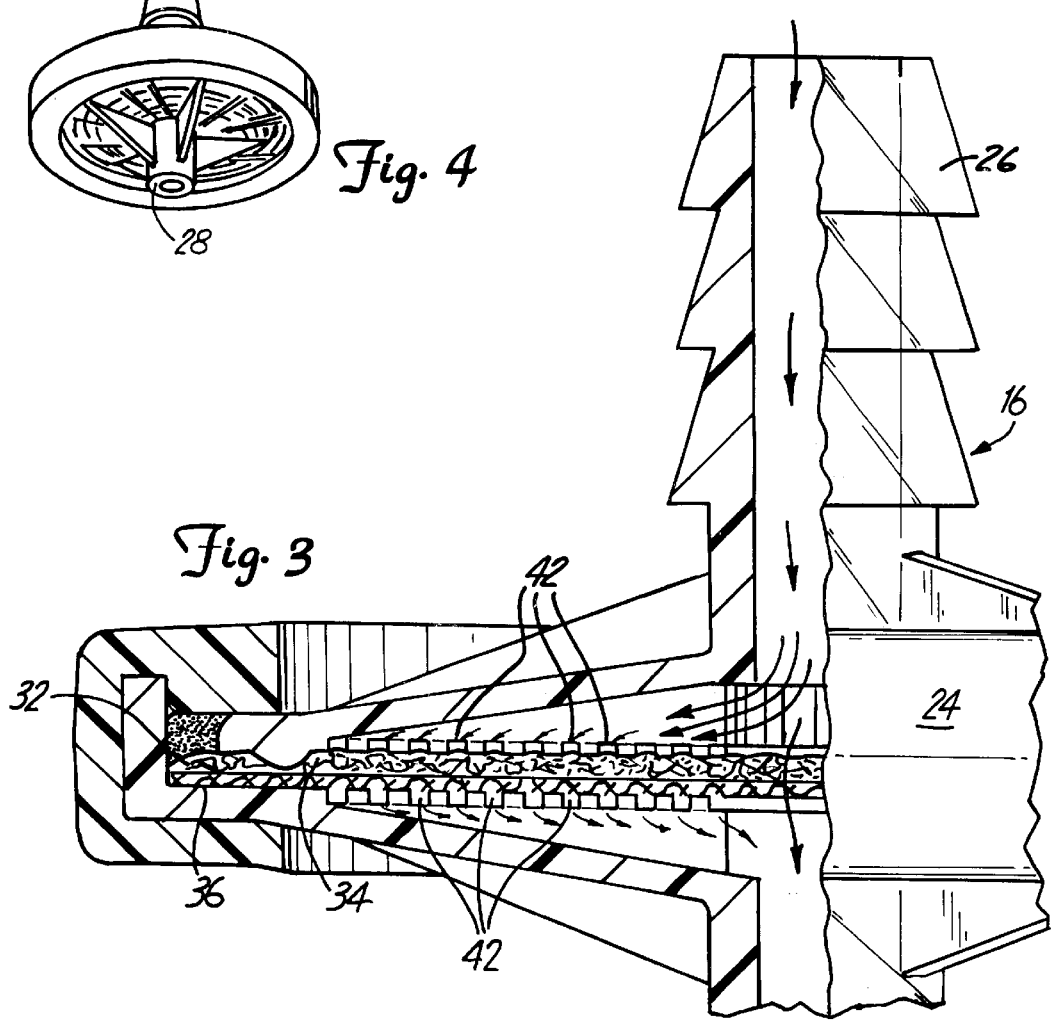
FIG. 3 depicts a portion of the filter of FIG. 2 in cross section.

Referring to FIG. 3, the filter 16 comprises a housing 24 with an inlet connector 26 and an outlet connector 28. Stepped hose barb type connectors may be used, as depicted in the Figures. The housing 24 may be made from polypropylene or other suitable material. The housing 24 contains the filter media 32, which comprises two thin, flat circular, disk shaped layers 34, 36. One layer 36, the layer adjacent to the outlet connector 28, is formed of 0.2 $\mu$m hydrophobic 200 mg/square cm PTFE, and the other layer 34 is made of a 200 g/square m 50% cellulose/carbon fiber blend. The layers 34, 36 are immediately adjacent to each other and each has a large surface area. Together, they form a filter media 32 having a surface area generally corresponding to its filtration area, i.e., approximately 7.5 square cm, approximately 100 times larger than the cross sectional area of the lumen of the depicted ¼ inch conduit 18. Although a disk-shaped filter is depicted, other shapes may be used as long as a pressure drop suitable for low flow, low pressure filtering is achieved. The filter 24, one or both layers, may be designed to exhibit a "change filter" color change indicative that useful life of the filter is over or nearly over. The odor removing layer 34 may be formed by or incorporate carbon or charcoal based material, or a diatomaceous earth material or other odor removing or reducing agent may be used.

Figure 4:
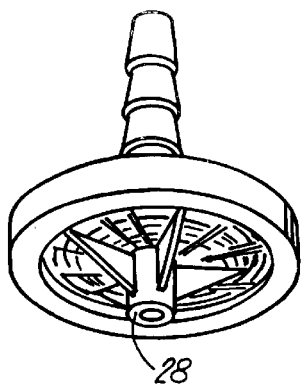
FIG. 4 depicts another embodiment of the filter.

The filter media 32 is potted or contained in the housing 24. The housing 24 has an inlet manifold 26 and an outlet manifold 28. On each side of the filter media 32, in the respective manifolds, the housing has a plurality of annular grooves 42. The housing 24 may be formed around the filter media 32, or it may be formed in pieces which are joined to pot the media 32. An alternative, button or rivet-like embodiment of the filter 16, wherein the outlet 28 is substantially reduced to an outlet port 28', is depicted in FIG. 4. This embodiment of the filter 16 may be carried at the free end of the conduit 18 or it, or a similar embodiment with a suitable protruding inlet connector for extending through the abdominal wall, may be coupled directly to the abdomen of a patient, for example, through a needle stick or other suitable opening.

Figure 12:
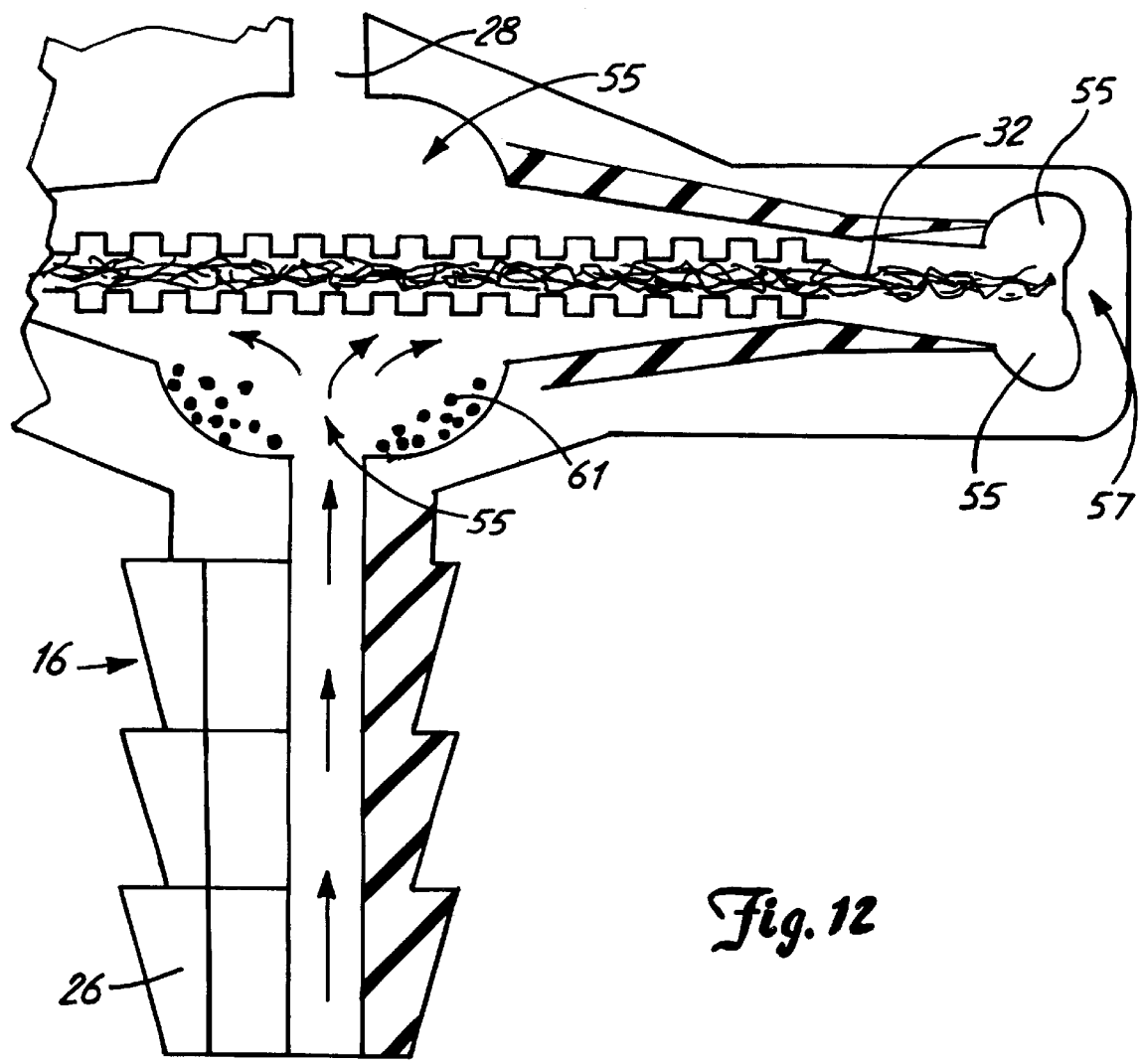
FIG. 12 depicts a portion of one embodiment of the filter of the invention in cross section.

Referring to FIG. 12, in one embodiment, a space 55 may be provided between the housing 24 and the filter media 32. This space 55, which may also be referred to as a water trap, provides an area in which moisture and/or condensed vapor may collect during use of the system and filter of the present invention. In some applications, such as high smoke, laser, or harmonic scalpel procedures, a substantial amount of water vapor may be produced along with smoke. Although the filter media 32 or filter paper may be made from hydrophobic material, in some high vapor-producing procedures, the filter media 32 may be unable to shed the water or vapor that condenses because there is little or no space or area for the moisture or liquid to move to and/or settle into. In an embodiment of the invention containing a space 55 between the filter media 32 and the housing 24, the space 55 provides an area or region in which water vapor can condense and settle without effecting the efficiency of the filter. FIG. 12 depicts one embodiment of a filter having a space 55 between the filter media 32 and the housing 24. The space 55 may be provided in a variety of orientations and locations with respect to the filter media 32 and the housing 24. For instance, the space 55 may be near the filter media 32 on the inlet 26 side of the housing 24 or, in other embodiments, on the outlet 28 side of the housing 24, or both. In addition, the space 55 may be near the outer and/or peripheral portions or regions 57 of the filter media 32 and housing 24. The space 55 may also have a variety of geometries in different embodiments of the invention, and it may be provided in one or more locations. In one embodiment of the invention, such as that depicted in FIG. 12, more than one space 55 may exist. FIG. 12, for instance, shows spaces 55 near the outer portions 57 of the housing, on the inlet side of the filter media 32, and on the outlet side of the filter media. This is advantageous because it provides for liquid collection spaces 55 which will be effective despite how the system may be positioned or oriented during a surgical procedure. FIG. 12 depicts condensed vapor 61 collecting in the space 55 near the inlet side of the filter media 32.

The system 14 provides a substantially unobstructed fluid flow path through the fluid conduit 18 between a valve 17 and filter 16 and, when the valve 17 is open, between a pressurized surgical site "S" and the filter 16. The filter 16 provides flow regulation of a fluid (insufflation gas carrying smoke) flowing along the fluid flow path in that it provides resistance to flow, whereby flow rates in some embodiments range from one (1) to four (4) liters/minute and, in other embodiments, range from 1 to 3.8 liters/minute. The filter 16 exhibits or has an associated pressure drop from one side to the other of from approximately one-half (0.5) to twenty (20) mm of mercury, with a pressure drop of from approximately two (2) to three (3) mm of mercury being preferred in another embodiment, and a pressure drop of approximately one (1) mm of mercury being preferred in yet another embodiment. The latter pressure drops correspond generally to flow rates of 1.8 liters/minute and 3.6 to 3.8 liters/minute, respectively. Higher pressures and/or lower pressure drops will produce higher correlative flow rates, and the filter 16 may be available in several specifications to be matched with the patient, function or procedure involved. The size and length of the fluid conduit or tube 18 may be varied to assist in providing desired flow characteristics (approximately 1.0 to 30 liters per minute) in conjunction with the resistance or pressure drop of the filter 16 of the present invention. The filter, therefore, may be designed for low flow applications, medium flow applications, or high flow applications. For instance, the filter 16 may operate at flow rates of about 0.2 to 30 liters per minute when coupled to pressurized surgical sites, wherein pressure drops of approximately 0.5 to 30 mm Hg exist.

In one embodiment, the invention may be a "passive" smoke evacuation system and method. In this embodiment, the filter 16 may be designed to regulate the flow of smoke and gases from a surgical site to the ambient air outside a patient's body without the use of a vacuum supply. The filter 16, in this embodiment, is designed to have a pressure drop at an associated flow rate sufficient to evacuate smoke from the pressurized cavity to the ambient air outside of the cavity without loss of pneumoperitoneum. For instance, in one embodiment, the filter 16 may have a resistance such that it causes a fluid flow rate of from approximately 0.2 to 30 liters per minute when coupled to a pressurized surgical site, wherein a pressure drop of approximately 0.5 to 30 mm Hg is maintained from the surgical site to ambient air, and wherein the fluid flow is induced as a result of the pressure in the pressurized surgical site. In other embodiments, the filter 16 may have a resistance such that a fluid flow rate of from about 1 to 20 liters per minute results at an associated pressure drop of from about 0.5 to 20 mm Hg.

In some embodiments, the tube 18 may be four to six feet in length, with a length of from 1.5 to 3.0 feet being preferred. If quarter inch tubing is selected, the lumen of the tube 18 typically would be 3 mm in diameter, but inner diameters ranging from 2 to 12 mm may be used. The parameters of diameter and length of tube 18, size of trocar (for one preferred example, 3 mm), and the resistance or pressure drop associated with filter 16 may be relatively adjusted to accommodate different patients, surgical procedures and/or operating room settings, as long as adequate low pressure, low flow smoke filtering and odor removal is achieved. The present invention may be embodied in a completely disposable, single use unit or components thereof, e.g., the filter or tubing, may be disposable with other component reusable. Typically, the trocar 20 or tubular member to which the conduit 18 is coupled, either directly or through an exhaust port or valve, is grounded to eliminate any errant current.

Figure 7:
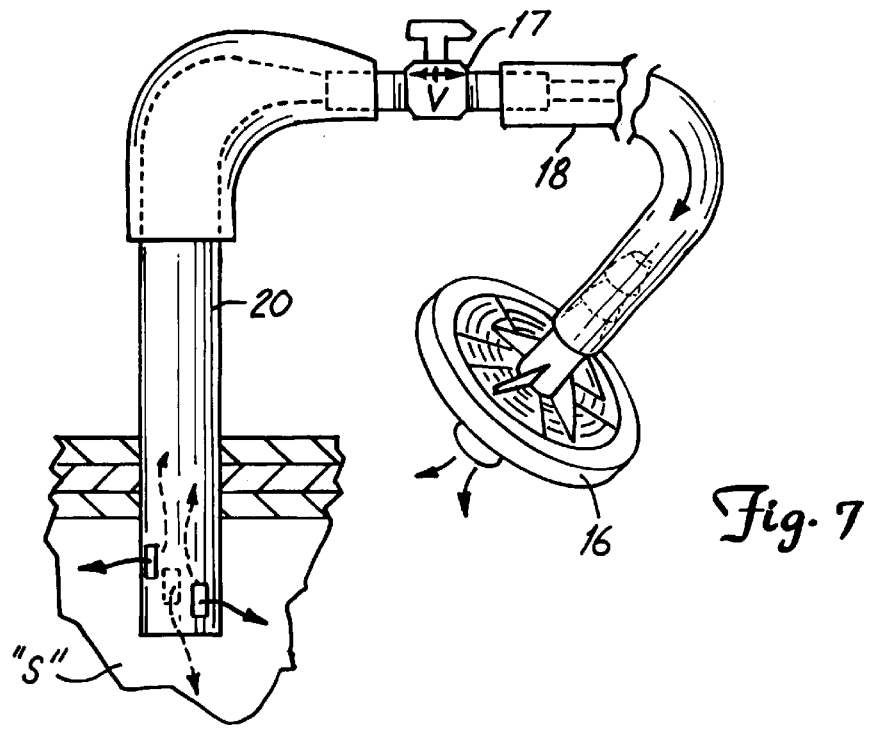
FIG. 7 depicts an elbow connector connecting a trocar and a valve connector.
Figure 6:
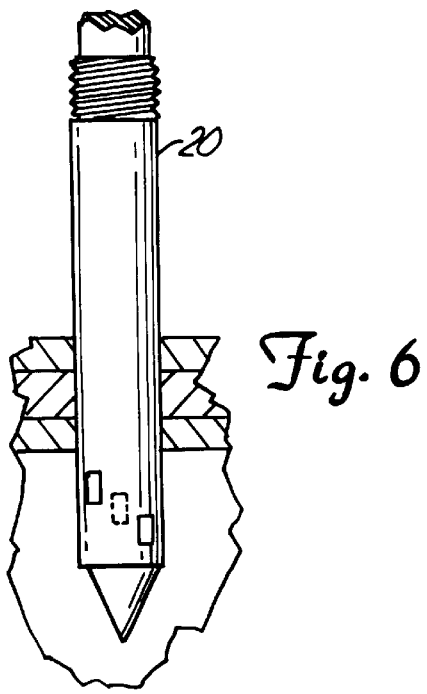
FIG. 6 depicts, largely representationally, a trocar (and obturator) of a type suitable for use with the present.

The present invention encompasses a method for evacuating smoke from a surgical site, particularly from a minimally invasive site such as a laparoscopy with a pneumoperitoneum. For example, for evacuating smoke from a surgical site in the abdominal cavity during a laparoscopic procedure, the method of the present invention comprises the steps of operably coupling a conduit 18 to the pneumoperitoneum, for example to the tubular member 21 (FIG. 7) extending from the pneumoperitoneum, and coupling a filter 16 having a low pressure drop there across to the conduit 18, whereby there is a substantially unobstructed, low volume fluid flow path between the pneumoperitoneum and the filter 16, whereby particulate material and odor are removed from the fluid. The fluid is induced to flow through the conduit 18 and filter 16 by the generally complementary pressure of the insufflating gas of the pneumoperitoneum and the pressure drop of the filter 16. In one embodiment, the flow may be controlled, e.g., initiated, stopped or reduced by incorporating a valve (such as a Leur lock valve (FIG. 5) or the like) with the conduit 18 or by using a valved trocar or the like.

The apparatus and method of the present invention may be used in laparoscopic procedure involving a pneumoperitoneum, i.e., a condition in which air or gas is collected or insufflated into the peritoneal cavity, but it also may be used in any other surgical procedure involving a substantially enclosed and/or pressurized surgical site such as thoracoscopy. Referring to FIG. 10, in one embodiment, the conduit 18 may be fitted with flow generating device 48 such as an in-line blower or impeller, which may be battery powered such as some commercially available models, for drawing air, smoke, particulate matter and contaminants into the conduit for filtration, whereby the invention may be used for "open" surgical procedures. In this embodiment, the selected flow generating device 48 may be located on either side of the filter 16, although positioning it on the outlet side of the filter 16 may protect it from contaminants and, in non-disposable embodiments, lengthen its useful life. The flow generating device 48 may be incorporated with the filter 16 itself, for example, in the outlet connector. With reference to FIGS. 9 and 10, for use in open site surgical procedures, the site or intake end of the conduit 18 may be expanded as at 19 and provided with a grille 21. In this embodiment the expanded end 19 may be, for example, inserted partially into a deep wound or connected to a patient's body near a surgical site (e.g., by using adhesive, straps, sutures or the like).

The present invention may be embodied in other specific forms without departing from the essential spirit or attributes thereof. It is desired that the embodiments described herein be considered in all respects as illustrative, not restrictive, and that reference be made to the appended claims for determining the scope of the invention.

What is claimed is:

1. A filter for use in surgical procedures, wherein the filter includes a housing surrounding a filter media with a space between the housing and the filter media shaped to trap condensation, the filter being adapted to be operably coupled to a pressurized surgical site and having a resistance such that a fluid flow rate of from approximately 0.2 to 20 liters per minute flows through the filter when the filter is coupled to the pressurized surgical site, wherein a pressure drop of approximately 0.5 to 20 mm Hg is maintained from the surgical site to ambient air, and wherein the fluid flow is induced as a result of the pressure in the pressurized surgical site.

2. The filter of claim 1, wherein the filter contains an inlet end and an outlet end with the filter media located within the housing between the inlet end and the outlet end, wherein the space is located between the inlet end and the filter media.

3. The filter of claim 1, wherein the filter contains an inlet end and an outlet end with the filter media located within the housing between the inlet end and the outlet end, wherein the space is located between the filter media and the outlet end.

4. The filter according to claim 1, wherein the filter has a resistance such that it exhibits a pressure drop of approximately 2 to 3 mm Hg at a fluid flow rate of approximately 1.8 liters per minute when coupled to the pressurized surgical site.

5. A smoke evacuating system for use during surgical procedures comprising a conduit adapted to be operably coupled to a pressurized surgical site and a filter adapted to be operably coupled to the conduit, the conduit forming a substantially unobstructed fluid flow path from the pressurized surgical site to the filter, the filter having a housing and filter media with a space between the filter media and the housing shaped to trap condensation and the filter having a surgical site side and an outlet side, wherein a fluid flow flows through the filter at a maintained pressure drop from the surgical site side to the outlet side, wherein the fluid flow is induced as a result of the pressure in the pressurized surgical site.

6. The smoke evacuating system of claim 5, wherein the filter media is circular and the space extends circumferentially around the filter media.

7. The smoke evacuating system of claim 5, wherein the housing of the filter surrounds the filter media and the space exists between the outlet side of the filter and the filter media.

8. The smoke evacuating system according to claim 5, wherein said fluid flows at approximately 1 to 30 liters per minute when the conduit and filter are coupled to the pressurized surgical site at a pressure drop ranging from approximately 0.5 to 30 mm Hg.

9. A smoke evacuating system for use during minimally invasive surgical procedures involving a pressurized surgical site having an associated higher than ambient pressure, said system comprising a filter with a housing and a filter media with a space between the housing and the filter media shaped to trap condensation, the filter having a site side and an outlet side and a fluid conduit extending between the pressurized surgical site and the filter, said fluid conduit defining a substantially unobstructed fluid flow path between the pressurized surgical site and filter, said higher than ambient pressure generating a fluid flow in the fluid flow path of approximately 0.2 to 30 liters per minute when coupled to the pressurized surgical site at a pressure drop of from approximately 0.5 to 30 mm Hg from the site side to the outlet side, wherein the fluid flow is generated substantially by the pressure in the pressurized surgical site.

10. The smoke evacuating system of claim 9, wherein the space is located to collect condensation from the filter media.

11. A method for evacuating smoke from a pressurized chamber, the method comprising:

coupling a filter to a hole in the pressurized chamber, wherein the filter has an associated fluid flow rate at a maintained pressure drop from the pressurized chamber to ambient air;

exhausting the smoke from the pressurized chamber through the filter by using air flow induced by the maintained pressure in the pressurized chamber;

aggregating condensed vapor from the smoke in the filter, wherein the filter includes a housing surrounding a filter media with a space between the housing and the filter media shaped to trap condensed vapor; and trapping condensed vapor in the space.

12. A smoke evacuating system comprising a filter having a site side and an outlet side and a fluid conduit extending there between, said fluid conduit having a filter media having a resistance such that a fluid flow rate of approximately 0.2 to 20 liters per minute flows through the filter when the filter is coupled to a pressurized surgical site with a pressure drop of approximately 0.5 to 30 mm Hg from the site side to the outlet side, said filter also having a space shaped and located to collect condensation from the filter.

* * * * *